United States Patent [19]
Botten et al.

[11] Patent Number: 5,609,585
[45] Date of Patent: Mar. 11, 1997

[54] WAFER HAVING ADHESIVE SKIN BARRIER LAYER

[75] Inventors: Ronald S. Botten, Gurnee; Larry R. DeCamp, Wauconda; Calla K. Stoick, Des Plaines; Eric D. Ellingson, Mount Prospect, all of Ill.

[73] Assignee: Hollister Incorporated, Libertyville, Ill.

[21] Appl. No.: 510,035

[22] Filed: Aug. 1, 1995

[51] Int. Cl.$^6$ .................................................. A61F 5/44
[52] U.S. Cl. ........................ 604/332; 604/336; 604/344
[58] Field of Search ........................ 604/336, 344; 428/152; 156/245; 128/156–157

[56] References Cited

U.S. PATENT DOCUMENTS

| | | | |
|---|---|---|---|
| 4,738,257 | 4/1988 | Meyer et al. | 128/156 |
| 4,867,748 | 9/1989 | Samuelson | 604/336 |
| 5,133,821 | 7/1992 | Jensen | 156/245 |
| 5,332,613 | 7/1994 | Taylor et al. | 428/152 |

*Primary Examiner*—Robert A. H. Clarke
*Assistant Examiner*—David J. Cho
*Attorney, Agent, or Firm*—Tilton Fallon Lungmus

[57] ABSTRACT

An adhesive wafer is disclosed having a thin barrier layer of soft, pliant adhesive material with particles of one or more hydrocolloids dispersed therein. A flexible and preferably stretchable cover layer extends along one side of the barrier layer and a removable release sheet protects the opposite side of the barrier layer. The wafer has a central zone and a relatively large outer zone surrounding that central zone, with the material of the barrier layer in the outer zone having generally uniform molecular orientations in radial directions over an arc of 360 degrees and being of relatively uniform tensile strength in all such radial directions. Also disclosed are injection/compression molding methods for making such wafers.

3 Claims, 5 Drawing Sheets

WAFER HAVING ADHESIVE SKIN BARRIER LAYER

BACKGROUND

Adhesive skin barrier materials are widely known in the medical field for use in ostomy faceplates, wound dressings, and skin-contacting gaskets or liners of various shapes and sizes, all of which may be generally referred to as hydrocolloid-containing wafers or dressings. A characteristic feature of such wafers is the presence of a skin-contacting layer of a soft, pliant adhesive material which has both dry and wet tack and which contains a dispersion of hydrocolloid particles capable of absorbing aqueous fluids and of swelling as such absorption takes place. One side of such a wafer usually has a cover layer of film or fabric, and the opposite side of the barrier layer is protected until use by a release sheet of siliconized paper or other suitable material. An example of one such wafer or dressing is disclosed in U.S. Pat. No. 4,738,257.

U.S. Pat. No. 4,738,257 discloses a wafer in which the hydrocolloid-containing adhesive layer is of substantially uniform thickness, but in recent years contoured wafers have become available in which the hydrocolloid-containing layers are not of uniform thickness. U.S. Pat. Nos. 5,133,821 and 4,867,748 disclose contoured wafers in which the hydrocolloid-containing barrier layers have relatively thick central body portions but then taper outwardly to terminate in peripheral edges or flanges of reduced thickness.

Whether contoured or not, all such wafers are believed to be produced in essentially the same way. A hydrocolloid-containing barrier material is simply extruded onto a web (which, following die cutting, may ultimately become the removable release sheet or the cover sheet for the finished wafer) and is then covered by a second web (which, following die cutting, may become the other outer layer for the wafer). If the wafers are to be contoured then, as disclosed in U.S. Pat. No. 5,133,821, the contouring operation may be undertaken prior to addition of the second web. Such contouring may be achieved by means of a roller (as in U.S. Pat. No. 5,133,821) or by a vertical press but, in either case, the contouring operation is performed on what is in effect a multi-layer sandwich in which the hydrocolloid-containing core layer of that sandwich has been extruded.

There are major disadvantages to a process requiring the extrusion of hydrocolloid-containing barrier materials, some of which have been well recognized in the past and others of which are only now being discovered. Skin barrier materials are generally expensive and substantial quantities of such materials are necessarily wasted because they become scrap in the final die-cutting operations. Wastage is particularly evident where the wafers are circular in outline, but such wastage also occurs to a substantial extent even for wafers of more rectangular shape.

Another disadvantage lies in the fact that making a contoured wafer with extruded barrier material is essentially a two step operation, the first step being the extrusion of a layer of barrier material of uniform thickness and the second step then being the compression of the barrier material into the desired contour. The requirement for successive processing steps provides its own complexities in terms of operating procedure and the physical size of the production equipment required. Additional problem areas involve keeping the freshly-extruded barrier material from sticking to the contouring roller. As disclosed in U.S. Pat. No. 5,133,821, a web of processing paper may be interposed between the barrier material and the contouring roller to prevent such sticking from taking place but, in that case, the processing web is generally stripped from the barrier after the contouring procedure and must be replaced by a web of different material which ultimately becomes the cover film of the final product. The need to use different web materials for processing (contouring) and for producing the final film (because the physical characteristics of the processing paper used for contouring may not be the properties desired as the outer film in the final product) presents additional complications and added expense.

In general, production methods for making adhesive wafers from extruded skin barrier materials require high-production equipment and long production runs with a minimum of interruptions. The very nature of such operations make quick changeover and interrupted operations difficult and impractical. The result is that specialized products of more limited demand, but nevertheless fulfilling important patient needs, may not reach the marketplace because production realities preclude their manufacture.

Figure 1:
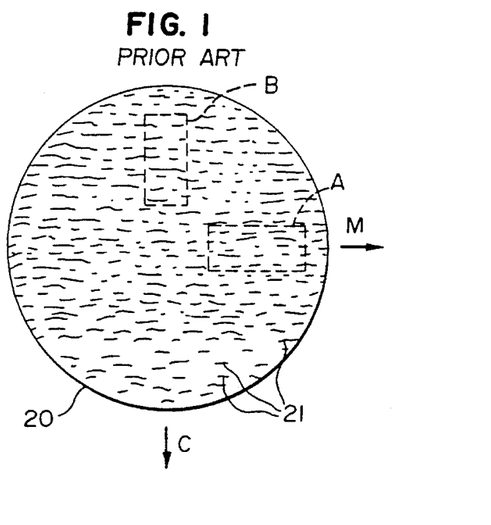
FIG. 1 is a plan view of the barrier layer of a conventional wafer produced by conventional extrusion techniques.

Finally, extrusion of skin barrier materials is now found to have a further disadvantage relating to the final products, their physical characteristics, and their performance. In the manufacture of extruded materials there is what is commonly known as "machine" direction and "cross" direction. The process of extrusion tends to orient molecules (also fibrous particles that may be included in the barrier composition) longitudinally in the direction of extrusion. Such parallel orientation means that properties that may be important in the performance of a wafer or dressing when it is used by a patient may not be uniform but instead may vary considerably depending on whether such properties are being measured in the machine direction or in the cross direction. For example, FIG. 1 depicts a barrier layer (exclusive of cover or release layers) of a conventional extruded wafer of uniform barrier thickness. The machine direction M is schematically illustrated by tiny striations oriented in parallel with the direction of extrusion, whereas the cross direction C is at right angles to the orientation of the striations. Such striations may take the form of filler particles of cotton or other fibrous additives, but such striations also represent the predominant direction of molecular orientation so that, even without the inclusion of a fibrous filler, properties in directions M and C tend to be different. Where such properties affect the strength of the barrier material (both prior to and following hydration), or the tendency to shrink in storage, or the rate of absorption or erosion, or the routes of saturation, swelling and/or leakage, the lack of uniformity in one direction versus another may have serious shortcomings.

SUMMARY OF THE INVENTION

This invention lies in the discovery that the production and product disadvantages arising from conventional extrusion techniques for making skin barrier wafers may be overcome by a combination of injection and compression molding procedures. It has now been discovered that the injection/compression molding of skin barrier wafers by our methods results in products having far more uniform physical characteristics (when measured in all radial directions in a 360 degrees arc about the centerpoint of a wafer) and also results in a production process that, in comparison with extrusion processes, has the advantages of being more economical with little or no wastage of barrier material, being easily adaptable for short production runs requiring only momentary downtime between runs, being ideally suited for successive runs in the manufacture of wafers of different sizes, shapes, and contours, being unlikely to present the sticking problems associated with the contouring of extruded wafers and the relatively expensive steps that have been taken in the past to avoid or reduce such sticking problems, and providing a relatively compact and efficient system for processing high quality wafers which may be combined with subsequent processing stations resulting in the production of finished articles, whether they be ostomy pouches equipped with such wafers, wound dressings, or other medical products.

Briefly, the method includes the steps of first depositing a mass or mound of soft, deformable skin barrier material (preferably heated to increase its flowability) onto a first web extending generally along a horizontal plane and supported by a rigid first platen beneath the web, subsequently or simultaneously locating a flexible second web a spaced distance above the first web and the mound with the second web backed by a rigid second platen positioned directly thereabove, and thereafter reducing the spacing between the first and second platens and compressing the mound of skin barrier material to displace a major portion of that material radially outwardly in directions extending 360 degrees about the original location of the deposit. At least one of the platens has a mold cavity of selected shape facing in the direction of the webs, with the cavity having an outline defining the shape of a wafer and the mound being located at the center of that cavity at the commencement of the compressing step. Wastage of barrier material is avoided or severely limited because only a predetermined amount of barrier material is deposited in the first step, such amount being sufficient only to cause displacement of the barrier material up to the outer limits, or possibly slightly beyond the outer limits, of the mold cavity during the compressing step.

Where the depositing and locating steps are performed simultaneously, the second web is provided with an aperture through which the skin barrier material is injected onto the receiving surface of the first web. In a preferred embodiment of the operating procedure, the step of locating the second web above the first web occurs immediately following the depositing step, the depositing step occurring at a first operating station and the web locating and compressing steps occurring at a second operating station. Because the depositing and compressing steps occur at different operating stations, it is therefore unnecessary to provide the second web with the injection aperture required by the other embodiment of the operating method.

The operation is intermittent but continuous with the webs being indexed forward and carrying the partially-finished wafers onto one or more subsequent processing stations. A final station involves the cutting of finished wafers from the web-barrier-web sandwich along the outer margins of the barrier layers, but other stations may also be involved. For example, a printing station (in which suitable indicia may be imprinted on one or both of the outer layers) may precede the cutting station. Also, while the finished wafers may be placed in storage for further processing, such additional processing may instead take place immediately following the cutting operation, with the barrier-manufacturing procedures constituting a part of a more encompassing manufacturing operation. For example, as each wafer is completed by the processing steps of this invention, it may be attached to a pouch to produce a finished ostomy appliance (or other type of collection appliance) and may then be packaged for distribution.

Other features, objects, and advantages of the invention will become apparent from the specification and drawings.

DETAILED DESCRIPTION OF PREFERRED EMBODIMENTS

Figure 2:
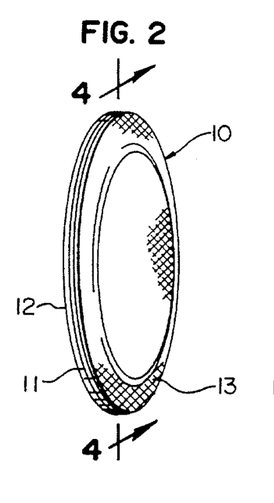
FIG. 2 is a perspective view of a typical wafer that may be produced by the injection/compression molding procedures of this invention.
Figure 4:
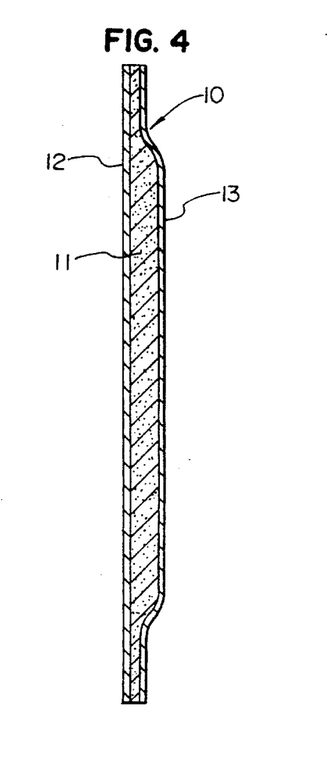
FIG. 4 is a sectional view taken along line 4—4 of FIG. 2.

In terms of appearance, wafers made in accordance with this invention may be outwardly similar to wafers made by conventional methods in which the barrier layers are extruded. Such wafers may be flat or contoured; may be circular, oval, trapezoidal or rectangular (the latter two shapes usually having rounded edges) in outline; may be flat or concave-convex in section; and may or may not have central openings. For example, FIGS. 2 and 4 depict a contoured wafer 10 having a core layer 11 of hydrocolloid-containing skin barrier material and outer layers 12 and 13. Layer 12 is a removable release sheet formed of siliconized paper or other suitable material, whereas layer 13 is a backing layer or cover layer that remains attached to the barrier layer as a permanent component of the wafer. The cover layer 13 may be composed of a polymeric film, such as polyurethane or polyethylene, or a woven or nonwoven fabric (porous or non-porous), or a layer of flexible polymeric foam (open cell or closed cell), or any other sheet materials having similar properties, or a combination of such materials. While a contoured wafer is shown in FIGS. 2 and 4, it is to be understood that the contour of any wafer made by the methods disclosed herein may be different than that shown or, if desired, may have planar side surfaces with no contour at all.

Figure 3:
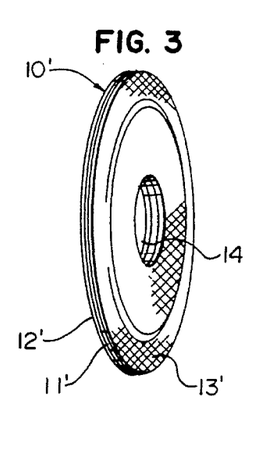
FIG. 3 is a perspective view of a typical wafer with a central opening that may be produced by the injection/compression molding procedures of this invention.

FIG. 3 shows a wafer 10' identical to the wafer 10 of FIG. 2 except for the provision of a central opening 14. In the following discussion, for purposes of illustration, outer layers 13, 13' will be considered as being formed of soft, microporous, nonwoven, heat-sealable fabric and layers 12, 12' will be considered as being formed of siliconized release paper but, as explained, the character of the materials used for these layers may be varied depending on the requirements for and the intended uses of the finished wafers.

The term "skin barrier" material is widely used in the medical field to refer to any of a variety of materials in which a sticky, pliant adhesive composition constitutes a continuous phase and particles of one or more liquid-absorbing and swellable hydrocolloids are dispersed throughout the adhesive and constitute a discontinuous phase. The adhesive phase commonly contains polyisobutylene, often in combination with one or more tackifiers, plasticizers, and antioxidants. An elastomer such as a styrene-isopyrene-styrene block copolymer (e.g., "Cariflex" TR-1107, from Shell Chemical Co.) or a styrene-butadiene-styrene block copolymer (e.g., "Kraton" 1100 Series, from Shell Chemical Co.) may be included, and other ABA block copolymers, such as ethylene-propylene block copolymers known as EPR rubbers have also been included in adhesive compositions for increasing the elastomeric properties of such barrier materials.

The discontinuous phase may be particles of any suitable hydrocolloid or mixtures of hydrocolloids such as sodium carboxymethylcellulose, calcium carboxymethylcellulose, pectin, gelatin, and natural gums such as gum guar, gum arabic, locust bean gum, karaya, and the like. Such hydrocolloids are water-absorbing and water-swellable. They absorb moisture from the skin and contribute to the wet tack characteristics of the skin barrier material, all as well known in the art.

When such a skin barrier material becomes hydrated, its consistency becomes more gel-like and a phase change usually takes place. The water and hydrated hydrocolloids convert to become the continuous phase and the water-insoluble adhesive components, such as the polyisobutylene, become the discontinuous phase. Regardless of the stage of hydration, and even prior to hydration, it is important that the physical characteristics of a wafer be similar in all radial directions. One easily-measured parameter is tensile strength, but other related characteristics such as shrinkage in storage, expansion on hydration, erosion in the presence of aqueous fluids, and absorption of such fluids of a skin barrier wafer should under ideal circumstances also be similar in all radial directions.

As indicated by tensile strength measurements, it is now believed that such objectives are achieved far more effectively by a wafer made by the injection/compression molding methods disclosed herein than a wafer composed of the same skin barrier material made by a conventional extrusion process. The differences in one parameter, tensile strength, are reflected by the charts of FIGS. 7 and 8 and by the explanatory schematics of FIGS. 1, 5 and 6.

FIG. 1 shows a disc 20 of skin barrier material formed by conventional extrusion techniques. M represents the machine direction and C designates the cross direction, with striations 21 schematically depicting the molecular orientation that tends to result from the extrusion process. Such orientations are predominately in the direction of flow.

Figure 5:
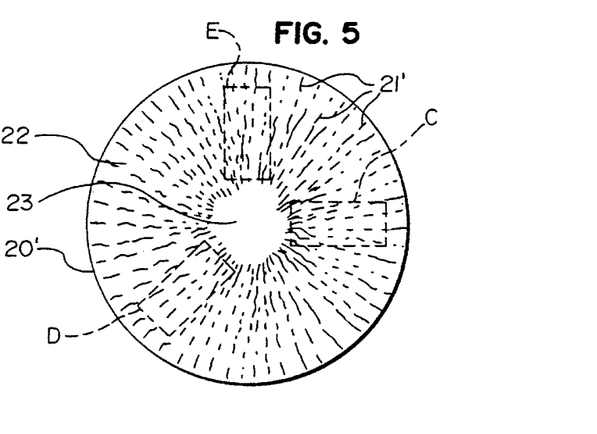
FIG. 5 is a schematic plan view similar to FIG. 1 but showing the planar barrier layer of a wafer embodying this invention and made by the method(s) disclosed herein.

FIG. 5 shows a similar barrier disc 20' made in accordance with the process depicted in FIGS. 9–13 but with the outer layers removed, leaving only the barrier layer of substantially uniform thickness. Radially extending striations 21' schematically depict a generally uniform molecular orientation in radial directions of flow over an arc or sweep of 360 degrees in what constitutes a relatively large annular outer portion or zone 22 of the disc. It is believed that in the relatively small central region 23 (or region at the center of mass) of the disc, the molecules may be more randomly oriented for reasons that will become apparent as the specification proceeds.

The differences in the tensile characteristics of the respective barrier discs when measured in different radial directions will become evident from the following illustrative examples:

EXAMPLE 1

Samples of extruded barrier material were compared with samples of the same barrier material made by the process of this invention. The barrier material was a commercial composition marketed under the designation "Guardian" by Hollister Incorporated, Libertyville, Ill. Such barrier material contains polyisobutylene as the primary adhesive in which particles of selected hydrocolloid materials are dispersed. A small quantity, less than 9% by weight, of cotton fibers are also included to provide greater internal strength. Such barrier composition is commercially used for ostomy appliances and effectively absorbs moisture and stomal fluids. Its elastomeric properties are not as great as some other skin barrier materials, although discs formed of "Guardian" barrier composition are flexible and pliant.

Rectangular samples corresponding to A, B, C, D and E and measuring 1.0 by 2.0 inches were cut as depicted on discs 20 and 20' in FIGS. 1 and 5. Ten samples A of extruded barrier material were cut with their greater dimension extending in the machine direction, and ten samples B of extruded barrier material were cut with their greater dimension extending in the cross direction.

Three samples of identical size (1.0 by 2.0 inches) were cut from each of ten discs 20', making a total of ten each of samples C, D and E as represented in FIG. 5. As shown therein, samples C and E extended radially at 90° with respect to each other, and sample D of each disc 20' extended radially at 45° in relation to the projected longitudinal axes of samples C and E.

Figure 7:
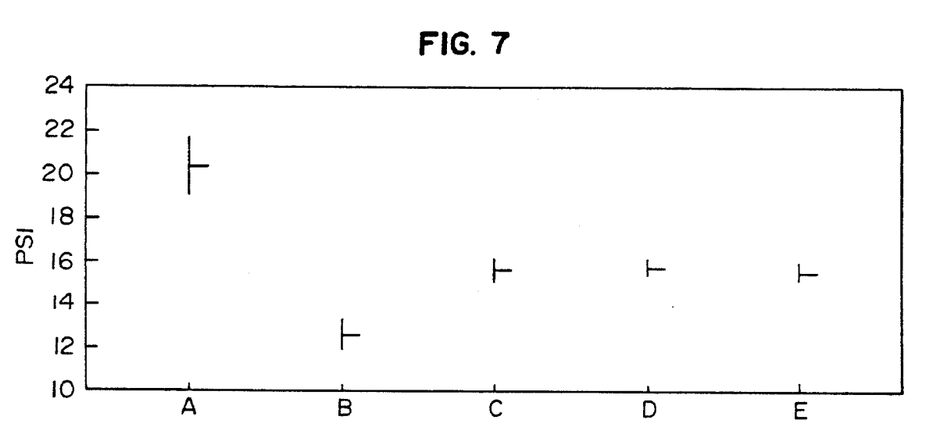
FIG. 7 is a chart showing the tensile stress characteristics at 10 percent elongation comparing skin barrier samples of the same composition, one batch being made by a conventional extrusion method and the other batch being made by the injection/compression molding method of this invention.

FIG. 7 plots the tensile stress measurements of all samples at 10% elongation using an Instron Series IX Automated Materials Testing System 6.05. The jaws of the machine gripped the ends of each sample at an initial distance of 1 inch apart (so that the "tested" portion of each sample measured 1.0 by 1.0 inches), and such jaws were then separated at a crosshead speed of 2.5 inches per minute.

Although the thickness of the samples cut from the extruded material were slightly thinner than the samples cut from the injection/compression molded materials (0.069 and 0.070 inches, respectively), all tensile stress measurements allowed for that difference by being computed in pounds per square inch (psi).

Figure 6:
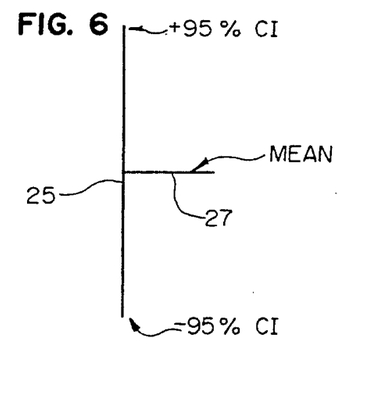
FIG. 6 is a key for analyzing the charts of FIGS. 7 and 8.
Figure 8:
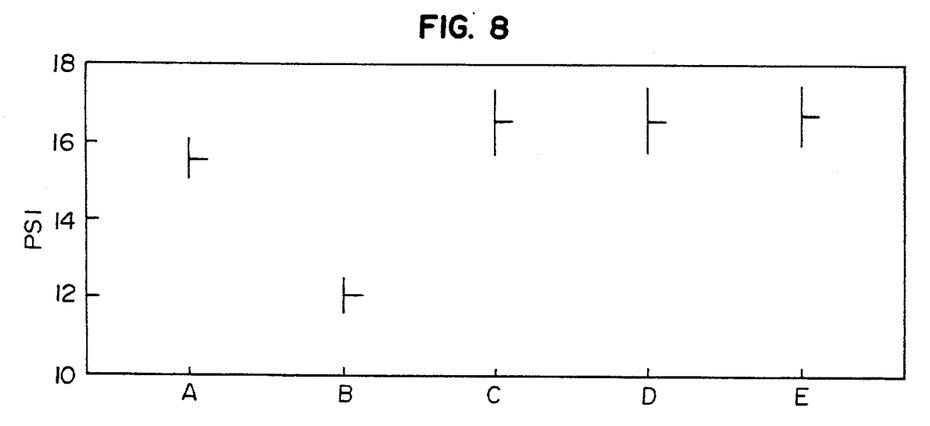
FIG. 8 is a chart showing the tensile stress characteristics at 100 percent elongation comparing skin barrier samples of the same composition (but different than the composition of FIG. 7), one batch being made by a conventional extrusion method and the other being made by the injection/compression molding of this invention.

FIG. 6 is a key that explains the characters appearing in the charts of FIGS. 7 and 8. In each case, the vertical line 25 represents what is referred to statistically as the "confidence interval" with its upper and lower limits representing the highest psi and the lowest psi for 95% of the samples in any given batch of samples A through E, respectively. Line 27 is the mean psi for any given batch.

The chart reveals that the full range of tensile stress measurements of extruded Guardian barrier samples A tested in the machine direction was far above the full range of tensile stress measurements for samples B tested in the cross direction. The mean tensile stress in the cross direction was 12.6 psi for samples B in contrast to a mean of 20.4 psi for extruded samples measured in the machine direction, the difference therefore being 7.8 psi. In contrast, the samples cut from injection/compression molded discs 20' at 0° (E), 45° (D) and 90° (C) were similar, with the maximum difference in the mean measurements for the samples of the respective batches C, D and E being no more than 0.2 psi.

EXAMPLE 2

A test similar to that described in Example 1 was conducted using a more elastomeric barrier material available as "Flextend" from Hollister Incorporated, Libertyville, Ill. Unlike "Guardian," such material contains no cotton fibers or any other fibrous filler. Tensile stress was measured for all of the samples at 100% elongation. Again, with respect to the extruded samples, no overlap in any of the tensile stress measurements between the 10 samples of batch A (measured in the machine direction) and those of batch B (measured in the cross direction) occurred. The difference in the mean tensile stress figures for those two batches was 3.5 psi. By contrast, the maximum difference between the mean tensile stress figures for samples C, D and E was only about 0.25 psi.

The results of the tensile strength tests described in Examples 1 and 2 and illustrated in FIGS. 7 and 8 therefore reveal that skin barriers made in accordance with the procedures disclosed herein result in discs in which the strength characteristics of the barrier materials in different radial directions are substantially the same, in contrast to large differences that exist when an extruded barrier is measured radially in machine and cross directions. Such uniformity of barriers made by the injection/compression molding procedures of this invention is believed to be associated with greater uniformity in radial directions of other characteristics that are important in barrier behavior and performance. For example, barrier materials are often subject to shrinkage in storage and it has been noted that with extruded barriers such shrinkage tends to be greater in a machine direction than in a cross direction. For a circular barrier of extruded material, that means that shrinkage will tend to be greater in one radial direction than another, whereas in a barrier embodying this invention, shrinkage is observed to be more uniform. Greater uniformity in other characteristics, such as fluid migration, swelling, absorption, and erosion is also believed to be more uniform in all radial directions than for extruded barriers, although the full extent thereof is not completely known.

With respect to molecular orientation, the data appearing in FIG. 8 would suggest that the molecules of injection/compression molded barriers tend to be oriented in radial directions, since the vertical lines for sample batches C, D and E all extend above the vertical lines for batch A, meaning that the strength in all radial directions for hydrocolloid discs made in accordance with our process equals or exceeds the strength of a conventionally extruded disc in its machine direction—its strongest direction. The same observation cannot be made for the data appearing in FIG. 7, but one important fact is evident from both figures, namely, that unlike an extruded barrier disc, discs formed by our process have an important physical characteristics (tensile strength) which relates directly to molecular orientation and which is substantially uniform in all radial directions (for 360 degrees) in the relatively large annular outer zone 22 of the barrier disc 20'.

Figure 9:
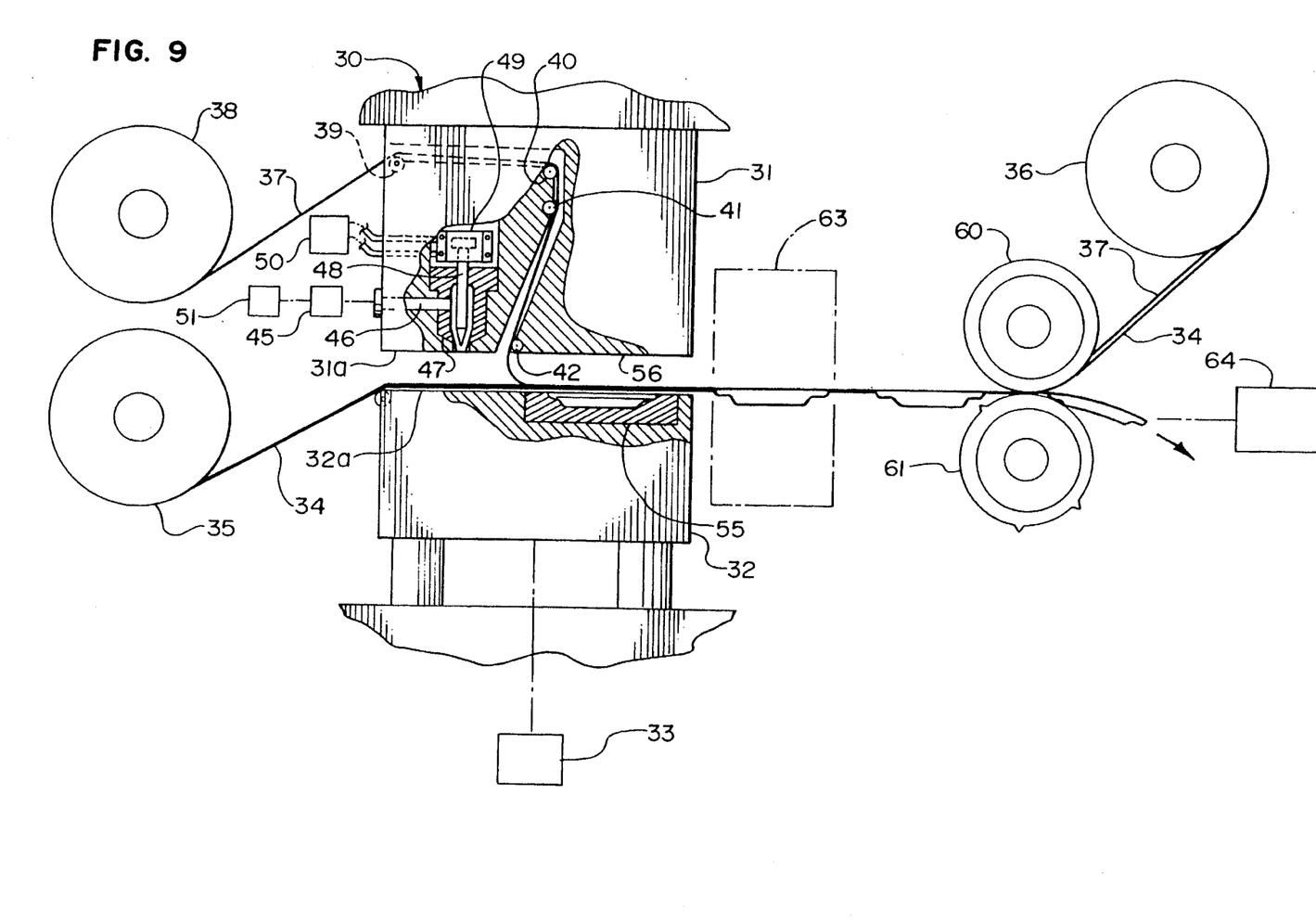
FIG. 9 is a schematic view illustrating equipment for carrying out the method of this invention.

Referring to FIG. 9, the numeral 30 generally designates an apparatus for carrying out the process of this invention. The machine includes a stationary upper platen member 31 and a vertically-movable lower platen member 32. Hydraulic means 33, or other suitable driving means, intermittently raise and lower member 32, with the spacing between the generally horizontal opposing faces 31a and 32a of the respective members being shown at maximum distance in FIG. 9. A web 34 from supply roll 35 extends across the face of the lower member and is ultimately re-rolled onto take-up roll 36. A second web 37 leads from supply roll 38 and over guide rollers 39–42 carried by the upper member, the web 39 then passing into the space between the two members and finally being rewound onto take-up roll 36. (Webs 34 and 37 are schematically shown slightly spaced apart adjacent the take-up roll only for clarity of illustration.).

Two sequential operating stations are provided by machine 30, the first station being an injection station in which a measured amount of barrier material is deposited onto the first web 34 and the second station being a compression molding station in which the deposited mass of barrier material is pressed into a desired shape between the first web 34 and the second web 37.

The operating elements at the injection station are conventional although their functions in carrying out the method of this invention are believed unique. Driving means 45 directs heated barrier material through passage 46 to nozzle 47. A gate valve 48 operated by air cylinder 49 and compressor 50, or by any other suitable means, intermittently raises and lowers the valve to allow measured quantities of barrier material to be discharged from the nozzle onto the lower first web 34 removably supported on the horizontal upper surface of member 32. The barrier material is stored and heated in a suitable reservoir 51. Heating increases the flowability of the barrier material, although the optimum temperature depends on the particular formulation involved. In general, temperatures in the range of 120° to 260° F. are believed effective.

At the compressing station, at least one of the members 31, 32 is provided with a die having a cavity in the shape of the wafer to be formed. In FIG. 9, the die 55 is removably supported in a recess provided by the lower vertically-movable platen member 32. The upper platen member 31 is stationary and has a flat face 56 parallel with die 55. The arrangement shown is believed to be particularly advantageous, but it is to be understood that, if desired, the upper member might instead be provided with the removable die 55 or, alternatively, both the upper and lower members might be so provided. The arrangement shown especially useful for making contoured wafers of the type shown in FIGS. 2–4 in which only one side of each wafer is contoured or stepped and the opposite side is flat or planar.

Figure 10:
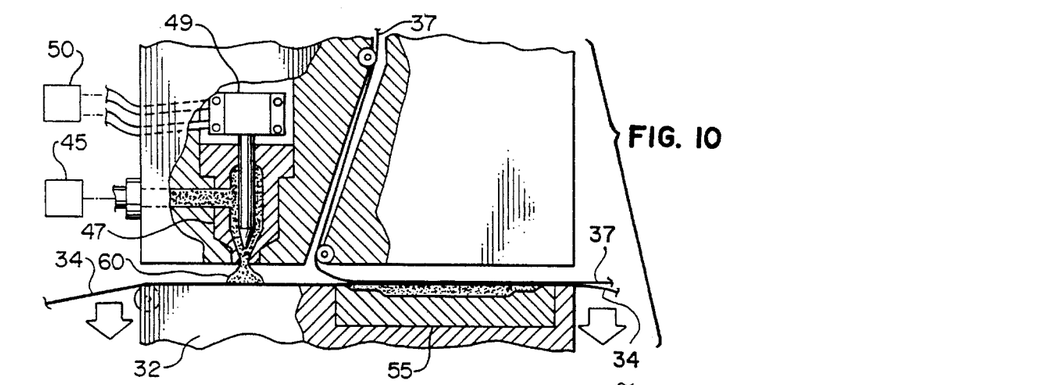
FIG. 10 is a first enlarged fragmentary view, shown partially in section, illustrating successive steps in performing the method of the is invention.
Figure 11:
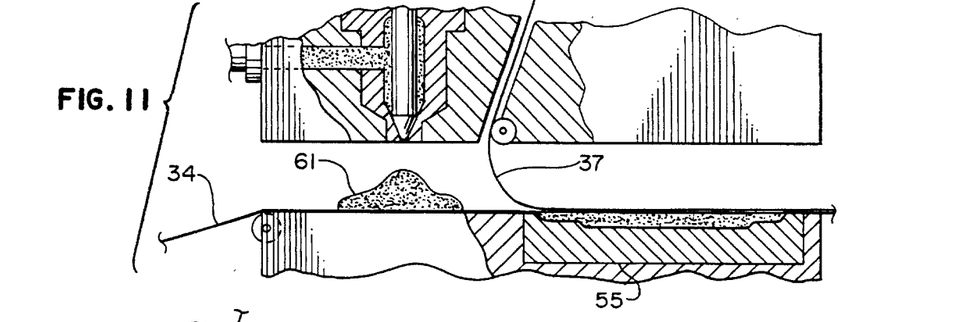
FIG. 11 is a second enlarged fragmentary view, shown partially in section, illustrating successive steps in performing the method of the is invention.

FIGS. 10–13 illustrate the sequence of steps in the injection/compression molding of barrier wafers. In FIG. 10, the valve gate is opened as platen member 32 commences its downward stroke. Heated barrier material 60 is discharged from the nozzle 47 onto the first web 34, and such discharge continues until the spacing between the upper and lower members approaches its maximum. The valve then closes, leaving a mass or mound 61 of barrier material on web 34 (FIG. 11). It is to be noted that the second web 37 does not pass through the space in which the depositing of softened barrier material occurs but instead converges towards web 34 in an area beyond the first station.

With the upper and lower platen members at maximum spacing, the two webs 34 and 37 are indexed forwardly to shift the mound 61 of barrier material into a central position over die plate 55. Since the upper web 37 also indexes forwardly, the mound or mass of barrier material is now disposed between the two webs (FIG. 12).

Figure 12:
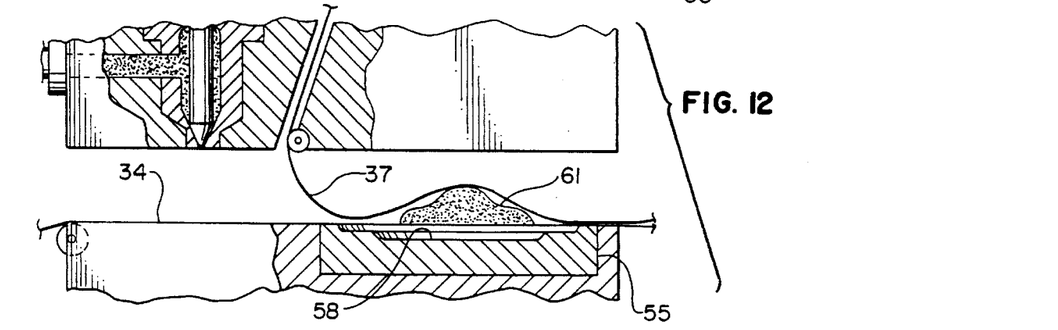
FIG. 12 is a third enlarged fragmentary view, shown partially in section, illustrating successive steps in performing the method of the is invention.
Figure 13:
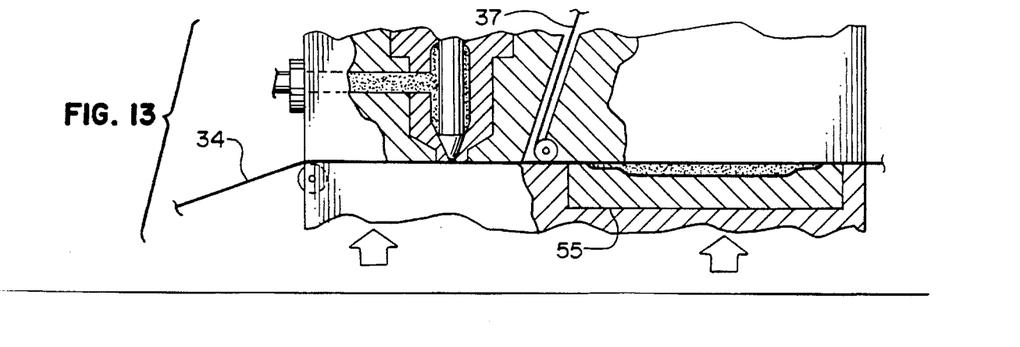
FIG. 13 is a forth enlarged fragmentary view, shown partially in section, illustrating successive steps in performing the method of the is invention.

At this point, drive means 33 operates to shift the lower platen member 32 upwardly to reduce the spacing and compress the barrier material so that it flows outwardly in all radial directions within the mold cavity 58 (FIGS. 12, 13). The quantity of barrier material in mound 61 may be precisely controlled so as to just fill, or almost fill, the cavity space available for it. The result is that wastage of barrier material during subsequent trimming operations is either completely eliminated or substantially avoided. Alternatively, the amount of barrier material may be controlled to slightly exceed the cavity space available for it, thereby causing a marginal flash of barrier material that must thereafter be trimmed away at a cutting station, but the amount of barrier so wasted would still be minimal and virtually insignificant in comparison with that commonly experienced in the die-cutting of extruded barrier materials.

The sequence is then repeated, with additional barrier material being deposited at the first station as the lower platen member 32 moves away from the upper platen member 31 (FIG. 10). The nearly finished wafer formed at the compression station is removed from that station in the indexing step immediately following FIG. 11.

Referring again to FIG. 9, the finished wafers 10 are cut from the incrementally advancing webs by cutting rollers 60, 61 or by any other suitable cutting means. The remainder of webs 34 amd 37 are wound onto take-up roller 36.

Other stations may be interposed between the compressing and cutting stations or may be located after the cutting station. For example, as represented by phantom lines 63 in FIG. 9, a printing station may be interposed between the compressing and cutting stations to print suitable indicia on one or both of the web portions that are to become the outer layers of the final wafers. Similarly, a processing station 64 may be located beyond the cutting station for attaching the wafers 10 to pouches or other articles, or for packaging the wafers into suitable wrappers, or for other processing operations. Stated differently, the injection/compression molding system depicted in FIG. 9, in combination with the cutting station and even the printing station 63, may be only the wafer-producing segment of a production line that then utilizes such wafers in making products in which the wafers are only a part.

In addition to avoiding or reducing waste of relatively expensive barrier material, the processing method disclosed herein has other important advantages over conventional extrusion methods. If, for example, it is desirable to interrupt the operation of the line to produce a quantity of wafers having a different contour, that may be accomplished simply by removing die 55 and replacing it with one having a cavity of different contour. Corresponding changes may or may not have to be made at the injection station and cutting station, depending on whether the quantities of barrier material required for each wafer are the same and whether the outer diameters of the wafers are unchanged but, in any case, the changes required and the time needed for making them are far less than commonly encountered in changing from one product to another in a conventional extrusion operation.

It is believed apparent that in the illustration given the material of web 37 ultimately becomes the releasable backing layer 12 for each of the finished wafers and that the material of web 34 becomes the covering layer 13 for each such wafer. As already indicated, such materials may vary considerably depending on product requirements but, in general, if a product is to be contoured as depicted in FIGS. 2–4, the material selected for the contoured side (or sides) of the wafer should be flexible and deformable so that it may readily assume the shape of the mold cavity at the compression molding station.

Figure 14:
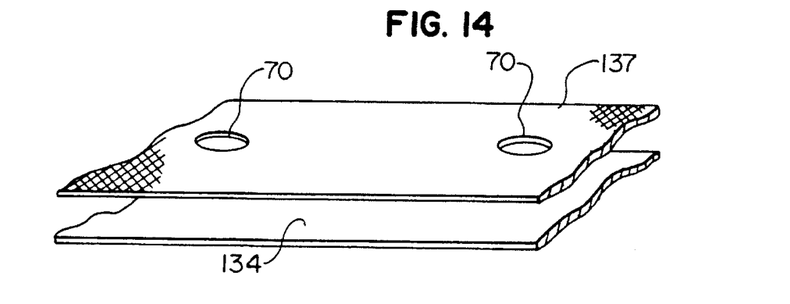
FIG. 14 depicts the web characteristics required for carrying out a production method constituting a second embodiment of this invention.

The injection and compression molding stations need not be spaced apart, even though the arrangement shown in FIGS. 9–13 is believed to be a preferred one. In a second embodiment depicted in FIGS. 14–16, the two stations are combined with both injection (depositing of barrier material) and compression (contouring of the barrier material by radial displacement) occurring without forward indexing of the webs.

Figure 15:
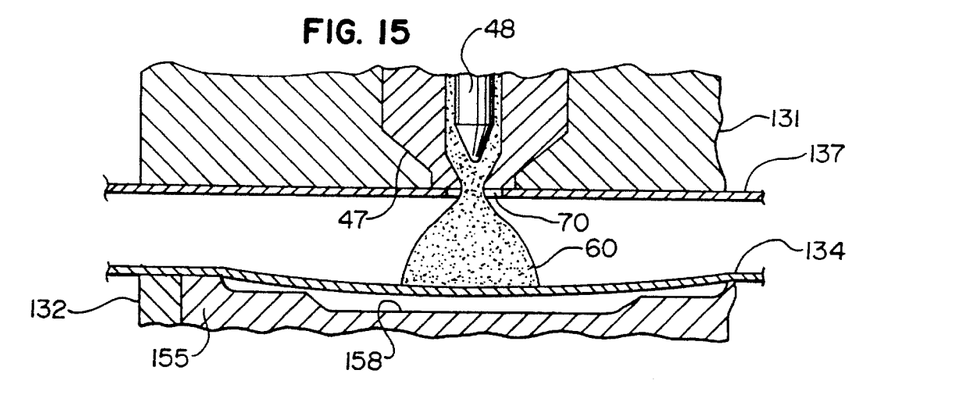
FIG. 15 schematically illustrates the simultaneous depositing and locating steps of the method constituting the second embodiment.

In the method of the alternate embodiment, the lower web 134 may be identical to web 34 already described, but the upper or second web 137, unlike web 37, has spaced apertures or openings 70. During the injecting step, heated barrier material 60 is discharged or dispensed through a web opening 70 by nozzle 47 (FIG. 15). When a mound of barrier material of sufficient volume has been discharged onto web 134, the lower platen member 132 is shifted upwardly towards the upper platen member 131 to close the spacing between the two platens and to force the barrier material radially outwardly in the directions of arrows 71 in FIG. 16.

The lower platen member is provided with a removable mold 155 having a cavity 158 which may be identical to mold 55 with its cavity 58, the only difference being that mold 155 is arranged so that its center is directly below the injection opening of the upper web 137, and below injection nozzle 47, so that no forward indexing is required between the injection and compression steps.

Figure 16:
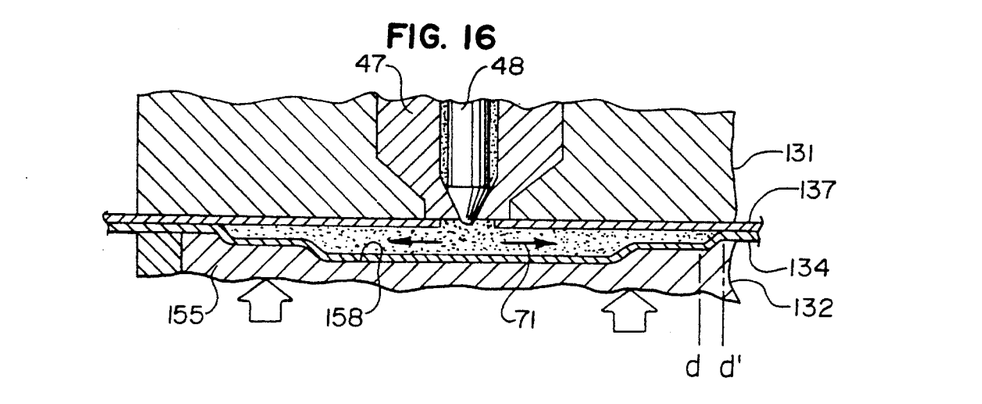
FIG. 16 depicts the compressing step of the second embodiment.

It is believed apparent that the method steps depicted in FIGS. 15 and 16 could alternatively be carried out with the injecting steps and the compressing steps occurring at different stations in the same manner as indicated with respect to the first embodiment. In that event, the only significant difference over the first embodiment would be that the upper web is perforated and passes through (rather than around) the injecting station, with barrier material then being discharged through the openings of the upper web in the manner depicted in FIG. 15.

Figure 17:
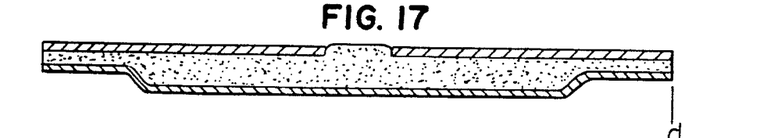
FIGS. 17 and 18 illustrate finished wafers which are identical to each other except for the location of the peripheral cut (that defines the outer edges of the wafers) in relation to the outer limits of the barrier layers.
Figure 18:
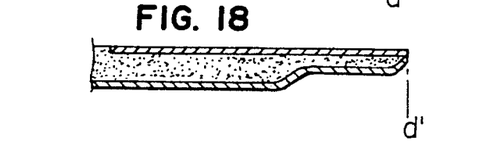

Whether there is wastage of barrier material during a cutting operation depends largely on the location of the cutting line. For example, FIG. 17 depicts a wafer having an outer perimeter die cut along cutting line "d" in FIG. 16. Barrier material extends to the cut edge of the finished wafer, and a slight amount of barrier material remains with the webs and must be discarded as scrap. On the other hand, if the cutting line is located further outwardly, at or just beyond the outer limits of the barrier material (as represented by "d" in FIG. 16), then there will be no wastage at all of barrier material and the finished product will have an appearance more similar to that depicted in FIG. 18. Under such conditions, the barrier material may terminate short of the outer limits of the wafer, and the outer layers of the wafer may contact each other beyond the peripheral limits of the barrier material.

While in the foregoing, we have disclosed embodiments of the invention in considerable detail for purposes of illustration, it will be understood by those skilled in the art that many of these details may be varied without departing from the spirit and scope of the invention.

We claim:

1. An adhesive wafer comprising (a) a thin barrier layer of soft, pliant, adhesive material having particles of one or more hydrocolloids dispersed therein and having upper and lower surfaces, (b) a flexible cover layer extending over one of said surfaces of said barrier layer, and (c) a removable release sheet extending over the other of said surfaces of said barrier layer; wherein the improvement comprises said wafer having a central zone and an annular outer zone; said material of said barrier layer in said outer zone being of generally uniform molecular orientations in radial directions over an arc of 360° about said central zone and being of substantially uniform tensile strength when measured in all of said radial directions.

2. The wafer of claim 1 in which the area of said outer zone is substantially greater than that of said central zone.

3. The wafer of claim 1 in which at least one of said surfaces of said barrier layer is contoured and said cover layer or said release sheet in contact therewith follows the contour of said barrier layer.

* * * * *